(12) United States Patent
Haley et al.

(10) Patent No.: US 7,709,448 B2
(45) Date of Patent: May 4, 2010

(54) PRODRUGS OF 5-AMINO-3-(3'-DEOXY-β-D-RIBOFURANOSYL)-THIAZOLO[4,5-D]PYRIMIDIN-2,7-DIONE

(75) Inventors: Gregory J. Haley, San Diego, CA (US); Joseph R. Lennox, San Diego, CA (US); Alan X. Xiang, San Diego, CA (US); Stephen E. Webber, San Diego, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 6 days.

(21) Appl. No.: 11/766,724

(22) Filed: Jun. 21, 2007

(65) Prior Publication Data

US 2008/0032999 A1 Feb. 7, 2008

Related U.S. Application Data

(60) Provisional application No. 60/815,576, filed on Jun. 22, 2006.

(51) Int. Cl.
*A01N 43/04* (2006.01)
*A61K 31/70* (2006.01)

(52) U.S. Cl. .................. 514/43; 514/42; 536/22.1; 536/27.1; 536/27.13; 536/27.2; 544/245; 544/255

(58) Field of Classification Search .................. None
See application file for complete search history.

(56) References Cited

U.S. PATENT DOCUMENTS

| | | | |
|---|---|---|---|
| 4,539,205 A | 9/1985 | Goodman et al. | |
| 4,643,992 A | 2/1987 | Goodman et al. | |
| 4,746,651 A | 5/1988 | Goodman | |
| 4,880,784 A * | 11/1989 | Robins et al. ............. | 514/48 |
| 5,011,828 A | 4/1991 | Goodman et al. | |
| 5,041,426 A * | 8/1991 | Robins et al. ............. | 514/43 |
| 5,041,542 A | 8/1991 | Robins et al. | |
| 5,166,141 A | 11/1992 | Goodman et al. | |
| 5,248,672 A | 9/1993 | Townsend et al. | |
| 5,395,937 A | 3/1995 | Nikolaides et al. | |
| 5,424,295 A | 6/1995 | Krenitsky et al. | |
| 5,446,045 A | 8/1995 | Revankar et al. | |
| 5,492,897 A | 2/1996 | Krenitsky et al. | |
| 5,821,236 A | 10/1998 | Krenitsky et al. | |
| 5,994,321 A | 11/1999 | Lewis et al. | |
| 6,028,076 A | 2/2000 | Hirota et al. | |
| 6,329,381 B1 | 12/2001 | Kurimoto et al. | |
| 6,376,501 B1 | 4/2002 | Isobe et al. | |
| 6,479,463 B1 | 11/2002 | Wang et al. | |
| 6,509,320 B1 | 1/2003 | Wang et al. | |
| 6,566,344 B1 | 5/2003 | Gosselin et al. | |
| 6,924,271 B2 | 8/2005 | Averett et al. | |
| 2002/0058635 A1 | 5/2002 | Averett | |
| 2002/0173655 A1 | 11/2002 | Dellaria et al. | |
| 2003/0065005 A1 | 4/2003 | Charles et al. | |
| 2003/0100764 A1 | 5/2003 | Bonk et al. | |
| 2003/0162806 A1 | 8/2003 | Dellaria et al. | |
| 2003/0176458 A1 | 9/2003 | Dellaria et al. | |
| 2003/0186949 A1 | 10/2003 | Dellaria et al. | |
| 2003/0195209 A1 | 10/2003 | Dellaria et al. | |
| 2003/0199461 A1 | 10/2003 | Averett et al. | |
| 2004/0063658 A1 | 4/2004 | Roberts et al. | |
| 2005/0004144 A1 | 1/2005 | Carson et al. | |
| 2005/0054590 A1 | 3/2005 | Averett | |
| 2005/0070556 A1 | 3/2005 | Averett et al. | |
| 2005/0182001 A1 | 8/2005 | Averett et al. | |
| 2006/0160830 A1 | 7/2006 | Webber et al. | |
| 2007/0117979 A1 | 5/2007 | Wang | |
| 2008/0020989 A1 | 1/2008 | Haley et al. | |
| 2008/0255063 A1 | 10/2008 | Averett et al. | |
| 2009/0197826 A1 | 8/2009 | Kucera et al. | |

FOREIGN PATENT DOCUMENTS

| | | |
|---|---|---|
| EP | 0882727 | 12/1998 |
| EP | 1035123 | 9/2000 |
| EP | 1043021 | 10/2000 |
| EP | 1386923 | 2/2004 |
| WO | WO-89/05649 | 6/1989 |
| WO | WO-92/16215 A1 | 10/1992 |
| WO | WO-94/07904 | 4/1994 |
| WO | WO-94/17043 | 8/1994 |
| WO | WO-94/17090 A1 | 8/1994 |
| WO | WO-98/17279 | 4/1998 |
| WO | WO-03/045968 | 6/2003 |

OTHER PUBLICATIONS

Vippagunta et al., Advanced Drug Delivery Reviews, 2001, 3-26.*
Akira, "Mammalian Toll-like receptors", *Current Opinion*, 2003, 15: 5-11.
Akira, "Toll-Like Receptor Signalling", *Immunology*, 2004, 4:499-511.
Alexander et al., "(Acyloxy)alkyl Carbamates as Novel Bioreversible Prodrugs for Amines: Increased Permeation through Biological Membranes", J. Med. Chem., 1988, 31:318-322.
Applequist et al., "Variable expression of Toll-like receptor in murine innate and adaptive immune cell lines", *Int. Immunol.*, 2002, 14(9):1065-74.

(Continued)

*Primary Examiner*—Traviss C McIntosh, III
(74) *Attorney, Agent, or Firm*—Connolly Bove Lodge & Hutz LLP; Mark J. Pino

(57) ABSTRACT

The invention is directed to 5-amino-3-(3'-deoxy-β-D-ribofuranosyl)-thiazolo[4,5-d]pyrimidin-2,7-dione prodrugs, whose metabolized parent compound has immunomodulatory activity. The invention also relates to the therapeutic use of such prodrugs and pharmaceutical compositions thereof in treating disease states associated with abnormal cell growth, such as cancer.

8 Claims, No Drawings

OTHER PUBLICATIONS

Barrio et al., "Regioselective Fluorination of Substituted Guanines with Dilute $F_2$: A Facile Entry to 8-Fluoroguanine Derivatives", *J. Org. Chem.*, 1996, 61:6084-6085.

Bottcher et al., "Differential regulation of Toll-like receptor mRNAs in experimental murine central nervous system infections", *Neurosci. Lett.*, 2003, 344(1):17-20.

Bruno et al., "Mouse pre-immunocytes as non-proliferating multipotent precursors of macrophages, interferon-producing cells, $CD8\alpha^+$ and $CD8\alpha^-$ dendritic cells", *Eur. J. Immunol.*, 2001, 31(11):3403-12.

Chuang et al., "Cloning and charactericaton of a sub-family of human Toll-like receptors: hTLR7, hTLR8 and hTLR9", *Eur. Cytokine Netw.*, Sep. 2000, 11(3):372-8.

Daskalov et al., Synthesis and Properties of O6-Substituted Guanosine Derivatives, Bull. Chem. Soc. Jpn., 54(10:3076-3083 (1981).

Diebold et al, "Innate antiviral responses by means of TLR7-mediated recognition of single-stranded RNA", *Science*, 2004, 303(5663):1481-2.

Doxsee et al, "The Immune Response Modifier and Toll-like Receptor 7 Agonist S-27609 Selectively Induces IL-12 and TNF-α Production in $CD11c^+CD11b^+CD8^-$ Dendritic Cells", *J. Immunol.*, 2003, 171(3):1156-63).

Du et al., *Eur. Cytokine Netw.*, 2000, 11(3), 362-71.

Edwards et al., "Toll-like receptor expression in murine DC subsets: lack of TLR7 expression by $CD8\alpha^+$ DC correlates with unresponsiveness to imidazoquinolines", *Eur. J. Immunol.*, 2003, 33(4):827-33.

Fan et al., "Pyrimidines. 24. Analogues and Derivatives of 2-Amino-5-bromo-6-phenyl-4(3*H*)- pyrimidinone (ABPP)", *J. Heterocyclic Chem.*, Nov. 1993, 30:1273-1276.

Fathi et al., "Synthesis of 6-Substituted 2'-Deoxyguanosine Derivatives Using Trifluoroacetic Anhydride in Pyridine", Tetrahedron Letters, 31(3):319-322 (1990).

Fried, et al., "5-Substituted 2-Amino-6-phenyl-4(3*H*)-pyrimidinones. Antiviral- and Interferon-Inducing Agents", *J. Med. Chem.*, 1980, 23:237-239.

Fujiwara et al., "Synthesis and Bioactivities of Novel Piperidylpyrimidine Derivatives: Inhibitors of Tumor Necrosis Factor-Alpha Production", *Bioorg. Med. Chem. Lett.*, 2000, 10(12):1317-1320.

Furneaux et al., "Improved Syntheses of 3*H*,5*H*-Pyrrolo[3,2-d]pyrimidines", *J. Org. Chem.*, 64 (22), 8411-8412 (1999).

Gangwar et al., "Synthesis of a Novel Esterase-Sensitive Cyclic Prodrug of a Hexapeptide Using an (Acyloxy)alkoxy Promoiety)", J. Org. Chem., 1997, 62:1356-1362.

Gibson et al., "Plasmacytoid dendritic cells produce cytokines and mature in response to the TLR7 agonists, imiquimod and resiquimod", *Cell Immunol.*, 2002, 218(1-2):74-86.

Girgis et al., "Direct C-Flycosylation of Guanine Analogues: The Synthesis and Antiviral Activity of Certain 7- and 9-Deazaguanine C-Nucleosides", J. Med. Chem., 1990, 33:2750-2755.

Goodman, "Role of Salvage and Phosphorylation in the Immunostimulatory Activity of C8-Substituted Guanine Ribonucleosides", J. Immunol., 14(7):2394-2399 (1988).

Hall et al., "Aldehyde Oxidase from Rabbit Liver: Specificity Toward Purines and Their Analogs", Archives of Biochemistry and Biophysics, 25(1):36-46 (1986).

Heil et al., "The Toll-like receptor 7 (TLR7)-specific stimulus loxoribine uncovers a strong relationship within the TLR7, 8 and 9 subfamily", *Eur. J. Immunol.*, 2003, 33(11):2987-97.

Hemmi et al., "Small anti-viral compounds activate immune cells via the TLR7 MyD88-dependent signaling pathway", *Nat. Immunol.*, 2002, 3(2):196-200.

Henry et al., "Synthesis and Broad-Spectrum Antiviral Activity of 7,8-Dihydro-7-methyl-8-thioxoguanosine", *J. Med. Chem.*, 1990, 33:2127-2130.

Hirota et al., "Discovery of 8-Hydroxyadenines as a Novel Type of Interferon Inducer", *J. Med. Chem.*, 2002, 45:5419-5422.

Horng et al., "The adaptor molecule TIRAP provides signaling specificity for Toll-like receptors", *Nature*, 2002, 420(6913):329-333.

Hornung et al., "Quantitative Expression of Toll-Like Receptor 1-10 mRNA in Cellular Subsets of Human Peripheral Blood Mononuclear Cells and Sensitivity to CpG Oligodeoxynucleotides", *J. Immunol.*, 2002, 168(9):4531-4537.

International Search Report (PCT/US2004/028236) dated Mar. 14, 2005.

International Search Report (PCT/US02/38001) dated Mar. 18, 2003.

Isobe et al, "Synthesis and Structure-Activity Relationships of 2-Substituted-8-hydroxyadenin Derivatives as Orally Available Interferon Inducers without Emetic Side Effects", *Bioorganic & Medicinal Chemistry*, 2003, 11:3641-3647.

Ito et al., "Roles of Toll-Like Receptors in Natural Interferon-Producing Cells as Sensors in Immune Surveillance", *Hum. Immunol.*, 2002, 63(12):1120-1125.

Jarrossay, "Specialization and complementarity in microbial molecule recognition by human myeloid and plasmacytoid dendritic cells", *Eur. J. Immunol.*, 2001, 31(11):3388-3393.

Jones et al., "Di- and Triester Prodrugs of the Varicella-Zoster Antiviral Agent 6-Methoxypurine Arabinoside", J. Med. Chem., 35(1):56-63 (1992).

Jurk et al., "Human TLR7 or TLR8 independently confer responsiveness to the antiviral compound R-848", *Nat. Immunol.*, 2002, 3(6):499.

Kerr et al, "Isatoribine, a Toll Like Receptor 7 Agonist, Significantly Reduced Plasma Viral Load in a Proof-of-Concept Study in Patients with Chronic Hepatitis C Virus Infection".

Kini et al., "Synthesis and Antiviral Activity of Certain Guanosine Analogues in the Thiazolo[4,5-*d*]pyrimidine Ring System", *J. Med. Chem.*, 1991, 34:3006-3010.

Krasny et al., "Metabolism and Pharmacokinetics of a Double Prodrug of Ganiclovir in the Rat and Monkey", Drug Metabolism and Disposition, 23(11):1242-1247 (1995).

Krasny et al., "Allopurinol as an Inhibitor of the in vivo Formation of Acyclovir from Desiclovir", Biochem. Pharm., 35(23):4339-4340 (1986).

Krenitsky et al., "6-Deoxyacyclovir: A xanthjne oxidase-activated prodrug of acyclovir", Proc. Natl. Acad. Sci., 81:3209-3213 (1984).

Krenitsky et al., "Xanthine Oxidase from Human Liver: Purification and Characterization", Archives of Biochemistry and Biophysics, 247(1):108-119 (1986).

Kurimoto et al., "Prodrugs of 9-Benzyl-8-hydroxy-2-(2-hydroxyethylthio)adenine: Potent Interferon Inducing Agents in Monkeys", *Chem. Pharm. Bull.*, 2004, 52(4):466-469.

Kurimoto et al., "Synthesis and evaluation of 2-substituted 8-hydroxyadenines as potent inferferon inducers with improved oral bioavailabilities", *Bioorg. Med. Chem.*, 2004, 12:1091-1099.

Le Quesne et al., "Biomimetic Synthesis of Catechol Estrogens" Potentially Mutagenic Arene Oxide Intermediates in Estrogen Metabolism, *J. Med. Chem*, 1980, 23:239-240.

Lee et al., "Molecular basis for the immunostimulatory activity of guanine nucleoside analogs: activation of Toll-like receptor 7", *PNAS*, 2003, 100(11): 6646-6651.

Lewis et al., "Thiazolo[4,5-*d*]pyrimidines. Part I. Synthesis and Anti-Human Cytomegalovirus (HCMV) Activity in vitro of Certain Alkyl Derivatives", J. Het. Chem., 32, 547-56, 1995.

Lore et al, "Toll-Like Receptor Ligands Modulate Dendritic Cells to Augment Cytomegalovirus-and HIV-1-Specific T Cell Responses", *J. Immunol.*, 2003, 171(8): 4320-4328.

Mealy, "ANA-971", *Drugs of the Future*, 2004, 29(5):507.

Mealy, "ISIS-14803—20-Mer antisense phosphorothioate oligodeoxynucleotide whose sequence is: 5'GTGCmTCmATG-GTGCmACmGGTCmT-3' where Cm represents 5-methylcytidine", *Drugs of the Future*, May 2004, 29(5):526-27.

Michael et al, "Alkylpurines as Immunopotentiating Agents. Synthesis and Antiviral Activity of Certain Alkylguanines", *J. Med. Chem.*, 1993, 36:3431-3436.

Miettinen et al., "IFNs activate toll-like receptor gene expression in viral infections", *Genes Immun.*, 2001, 2(6):349-355.

Mohty et al., "IFN-α Skews Monocyte Differentiation into Toll-Like Receptor 7-Expressing Dendritic Cells with Potent Functional Activities", *J. Immunol.*, 2003, 171(7):3385-93.

Nagahara et al., "Thiazolo[4,5-d] pyrimidine Nucleosides. The Synthesis of Certain 3-B-D-Ribofuranosylthiazolo[4,5-d]pyrimidines as Potential Immunotherapeutic Agents", J. Med. Chem., 33(1):407-415 (1990).

Nagase et al., "Expression and Function of Toll-Like Receptors in Eosinophils: Activation by Toll-Like Receptor 7 Ligand[1]", J. Immunol., 2003, 171(8):3977-3982.

O'Neill, "After the Toll Rush", Science, 2004, 303:1481-1482.

Okada et al., "Murine thymic plasmacytoid dendritic cells", Eur. J. Immunol., 2003, 33(4): 1012-9.

Pinhal-Enfield et al., "An Angiogenic Switch in Macrophages Involving Synergy between Toll-Like Receptors 2, 4, 7, and 9 and Adenosine $A_{2A}$ Receptors", Am. J. Pathol., 2003, 163(2):711-721.

Pockros et al., "A Phase IIa Placeob-Controlled, Double-Blind Trial to Determine the Safety, Tolerability, PK/PD of an Oral Interferon Inducer, Resiquimod, in chronic HCV", Gastroenterology, 2003, 124(Suppl 1): A-766.

Pockros "Attacking the Hepatitis C Virus with New Mechanisms of Action: Drugs in the Pipeline", The HCV Advocate: Medical Writer's Circle, May 2004, pp. 1-5.

Purifoy et al., "Review of Research Leading to New Anti-Herpesvirus Agents in Clinical Development: Valaciclovir Hydrochloride (256U, the L-Valyl Ester of Acyclovir) and 882C, a Specific Agent for Varicella Zoster Virus", Journal of Medical Virology Supplement, 1:139-145 (1993).

Raney et al, "HEP DART 2003: Frontiers in Drug Development for Viral Hepatitis", Expert Opin. Investig. Drugs, 2004, 13(3):289-293.

Reitz, et al., "Small-Molecule Immunostimulants. Synthesis and Activity of 7,8-Disubstituted Guasnosines and Structurally Related Compounds", J. Med. Chem., 1994, 37(21):3561-3578.

Revankar et al., "Synthesis and Antiviral/Antitumor Activities of Certain 3-Deazaguanine Nucleosides and Nucleotides", J. Med. Chem., 1984, 27:1389-96.

Revankar et al., "Thiazolo[4,5-d]Pyrimidines. Part II. Synthesis and Anti-human Cytomegalovirus Activity in Vitro of Certain Acyclonucleosides and Acyclonucleotides Derived from Guanine Analogue 5-Aminothiazolo[4,5-d]Pyrimidine-2,7(3H,6H)-dione", Antiviral Chemistry & Chemotherapy, 9:53-63 (1998).

Revankar et al., "Synthesis of Certain N- and C-Alkyl Purine Analogs", J. Het. Chem., 30, 1341-49 (1993).

Rhodes, "Discovery of immunopotentiatory drugs: current and future strategies", Clin. Exp. Immunol., 2002, 130:363-369.

Rida et al., "Synthesis of Novel Thiazolo[4,5-d]Pyrimidine Derivatives for Antimicrobial, Anti-HIV and Anticancer Investigation", Pharmazie, 51(12):927-931 (1996).

Rothenfusser et al., "Plasmacytoid Dendritic Cells: The Key to CpG", Hum. Immunol., 2002, 63(12):1111-1119.

Sato et al., "A variety of microbial components induce tolerance to lipopolysaccharide by differentially affecting MyD88-dependent and -independent pathways", Int. Immunol., 2002, 14(7):783-91.

Seela et al., :Alternative d(G-C)3 and d(C-G)3 Hexanucleotides Containing 7-Deaza-2'-deoxyguanosine or 8-Aza-7-deaza-2'-deoxyguanosine in Place of dG, Nucleic Acids Res., 17(3):901-910 (1989).

Seela et al., "Synthese von 2-Amino-2,7-dihydro-7-(β-D-ribofuranosyl)-4H-pyrrolo[2,3-d]pyrimidin-4-on—7-Desazaguanosin—der Stammverbindung des Nucleosids Q", Chem. Ber., 1981, 114 (10):3395-3402.

Skulnick et al., "Pyrimidinones. 3. N-Substituted 6-Phenylpyrimidinones and Pyrimidinediones with Diuretic/Hypotensive and Antiinflammatory Activity", J. Med. Chem., 1986, 29:1499-1504.

Smee et al., "Broad Spectrum In Vivo Antiviral Activity of 7-Thia-8-Oxoguanoine, a Novel Immunopotentiating Agent", Antimicrobial Agents and Chemotherapy, 33(9):1487-1492 (1989).

Smee et al., "Broad-Spectrum Activity of 8-chloro-7-deazaguanosine Against RNA Virus Infections in Mice and Rats", Antiviral Res., 26:203-209 (1995).

Townsend, "The Synthesis of 2-Amiono-7-β-D-ribofuranosyl)pyrrolo[2,3,d)-pyrimidin-4-one (7-Deazaguanosine), a Nucleoside Q and Q* Analog (1)", J. Heterocyclic Chem, Dec. 1976, 13:1363-1364.

Ulevitch, "Therapeutics Targeting the Innate Immune System", Nature, 2004, 4:512-520.

Wong et al., "Photochemical Synthesis of 8-Hydroxyguanine Nucleosides", Methods Enzymol., 234:59-65 (1994).

Yamamoto et al., "Cutting Edge: A Novel Toll/IL-1 Receptor Domain-Containing Adapter That Preferentially Activates the IFN-β Promoter in the Toll-Like Receptor Signalinig [1]", J. Immunol., 2002, 169(12):6668-72.

Yamamoto et al., "Essential role for TIRAP in activation of signaling cascade shared by TLR2 and TLR4", Nature, 2002, 420(6913):324-9.

"Oral Interferon-Like Molecule", Updated on New Experimental Therapies, <http://archive.mail-list.com/pkids/msg03975.html>, Jul. 21, 2004.

International Search Report and Written Opinion (PCT/US05/45589) dated May 18, 2006.

International Search Report and Written Opinion (PCT/US2007/21830) dated Jun. 23, 2008.

* cited by examiner

PRODRUGS OF 5-AMINO-3-(3'-DEOXY-β-D-RIBOFURANOSYL)-THIAZOLO[4,5-*D*]PYRIMIDIN-2,7-DIONE

This application claims the benefit of U.S. Provisional Application No. 60/815,576, filed Jun. 22, 2006.

FIELD OF THE INVENTION

The invention is directed to 5-amino-3-(3'-deoxy-β-D-ribofuranosyl)-thiazolo[4,5-d]pyrimidin-2,7-dione prodrugs, whose metabolized parent compound has immunomodulatory activity. The invention also relates to the therapeutic use of such prodrugs and pharmaceutical compositions thereof in treating disease states associated with abnormal cell growth, such as cancer.

BACKGROUND OF THE INVENTION

The last few decades have seen significant efforts expended in exploring possible therapeutic uses of guanine analogs and nucleosides thereof. A number of nucleoside analogs are currently being marketed as antiviral drugs, including HIV reverse transcriptase inhibitors such as AZT, ddI, ddC, d4T, 3TC and the guanosine nucleoside analog abacavir. While not adhering to a particular theory, nucleoside analogs may provide benefits by directly inhibiting the pathogen or tumor, by stimulation of host immune functions, or some combination of these or other mechanisms.

One of the studied guanosine analogs with demonstrated immunomodulatory activity is 5-amino-3-(β-D-ribofuranosylthiazolo[4,5-d]pyrimidine-2,7(3H, 6H)dione(7-thia-8-oxoguanosine). For example, certain pyrimido[4,5-d]pyrimidine nucleosides are disclosed in U.S. Pat. No. 5,041,542 to Robins et al. as being effective in treatment against L1210 in BDF1 mice. In addition, 3-β-D-ribofuranosylthiazolo[4,5-d]pyrimidines demonstrating significant immunoactivity, including murine spleen cell proliferation and in vivo activity against Semliki Forest virus, are disclosed U.S. Pat. Nos. 5,041,426 and 4,880,784 to Robins et al. A number of publications have also described non-glycosyl derivatives of the thiazolo[4,5-d]pyrimidine moiety. See, e.g., U.S. Pat. Nos. 5,994,321 and 5,446,045; Revankar et al., *J. Het. Chem.*, 30, 1341-49 (1993); Lewis et al., *J. Het. Chem.*, 32, 547-56 (1995).

SUMMARY OF THE INVENTION

The present invention describes novel 5-amino-3-(3'-deoxy-β-D-ribofuranosyl)-thiazolo[4,5-d]pyrimidin-2,7-dione prodrugs and pharmaceutically acceptable salts thereof, which are useful as immunomodulators. The invention also encompasses the therapeutic use of such prodrugs and compositions thereof in the treatment of disease states associated with abnormal cell growth, such as cancer.

In a general aspect, the invention relates to 5-amino-3-(3'-deoxy-β-D-ribofuranosyl)-thiazolo[4,5-d]pyrimidin-2,7-dione prodrugs of Formula I

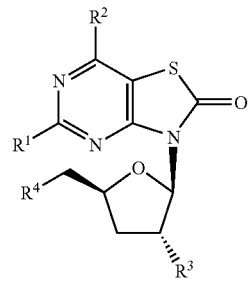

wherein $R^1$ is $NH_2$ or $-N=CHNR^6R^7$, $R^2$ is H, OH, or $-OR^5$, $R^3$ is OH, $-OC(O)C_1-C_{18}$alkyl, $-OCO_2R^5$, $-OC(O)NR^6R^7$, or a racemic, L-, or D-amino acid group $-OC(O)CHR^8NHR^9$, $R^4$ is OH, $-OC(O)C_1-C_{18}$alkyl, $-OCO_2R^5$, $-OC(O)NR^6R^7$, or a racemic, L-, or D-amino acid group $-OC(O)CHR^8NHR^9$, $R^5$ is $-C_1-C_7$alkyl, $R^6$ and $R^7$ are independently $-C_1-C_7$alkyl or together with nitrogen atom to which they are attached form a 5- or 6-membered heterocyclic ring, $R^8$ is H or $-C_1-C_7$alkyl, $R^9$ is H, $-C_1-C_7$alkyl, $-C(O)R^5$, or $-CO_2R^5$, wherein at least one of $R^3$ or $R^4$ is $-OCO_2R^5$, $-OC(O)NR^6R^7$, or a racemic, L-, or D-amino acid group $-OC(O)CHR^8NHR^9$, wherein the above alkyl is optionally substituted by 1-4 substituents selected from hydrogen,
alkylamine,
amino,
aryl, cycloalkyl, heterocyclyl,
$C_1-C_6$ alkyl, $C_1-C_6$ haloalkyl, $C_1-C_6$ hydroxyalkyl, $C_1-C_6$ alkoxy, $C_1-C_6$ alkylamine, $C_1-C_6$ dialkylamine, $C_2-C_6$ alkenyl, or $C_2-C_6$ alkynyl, wherein each of which may be interrupted by one or more hetero atoms,
carboxyl,
cyano,
halo,
hydroxy,
mercapto,
oxo,
thioalkyl,
$-C(O)_2-(C_1-C_6$ alkyl), $-C(O)_2$-(aryl), $-C(O)_2$-(cycloalkyl), $-C(O)_2$-(heterocyclyl), $-O-(C_1-C_6$ haloalkyl), $-O$-aryl, $-O$-heterocyclyl, $-NHC(O)-(C_1-C_6$ alkyl), $-NHC(O)-(C_1-C_6$ alkenyl), $-NHC(O)$-(aryl), $-NHC(O)$-(cycloalkyl), $-NHC(O)$-(heterocyclyl), $-NHS(O)_2-(C_1-C_6$ alkyl), $-NHS(O)_2$-(aryl), $NHS(O)_2$-(cycloalkyl), and $-NHS(O)_2$-(heterocyclyl), wherein each of the above substituents can be further optionally substituted by 1-5 substituents selected from
amino,
$C_1-C_6$ alkylamine, $C_1-C_6$ dialkylamine, $C_1$-$C_6$ alkyl, $C_1$-$C_6$ alkoxy, $C_1$-$C_6$ alkenyl, $C_1$-$C_6$ hydroxyl, and $C_1$-$C_6$ hydroxyalkyl, each optionally substituted by cyano, halo, and nitro, or a pharmaceutically acceptable salt, hydrate, or stereoisomer thereof In another embodiment, the invention relates to compounds of Formula I, wherein $R^2$ is H or OH.

In another embodiment, the invention relates to compounds of Formula I, wherein $R^3$ is —OCO$_2$R$^5$ or —OC(O)NR$^6$R$^7$ and $R^4$ is OH, —OC(O)C$_1$-C$_{18}$alkyl, —OCO$_2$R$^5$, or —OC(O)NR$^6$R$^7$.

In another embodiment, the invention relates to compounds of Formula I wherein $R^4$ is —OCO$_2$R$^5$ or —OC(O)NR$^6$R$^7$ and $R^3$ is OH, —OC(O)C$_1$-C$_{18}$alkyl, —OCO$_2$R$^5$, or —OC(O)NR$^6$R$^7$.

In another embodiment, $R^5$ is isopropyl.

In another embodiment, $R^6$ and $R^7$ are independently methyl or ethyl.

In another embodiment, the invention relates to compounds of the Formula I selected from

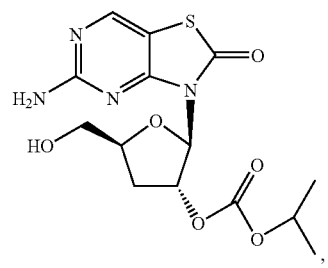

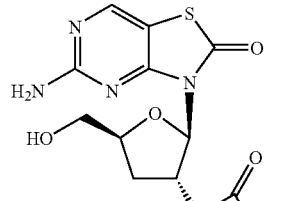

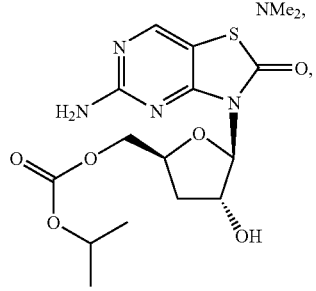

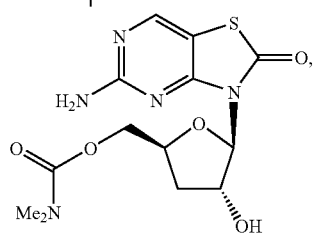

-continued

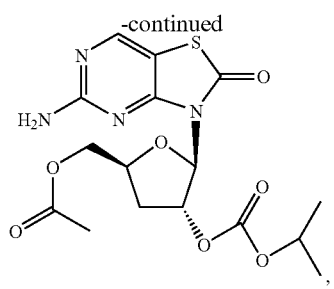

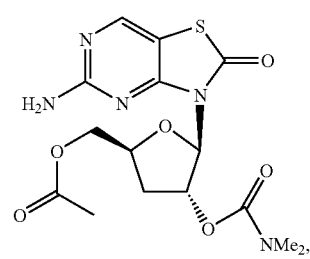

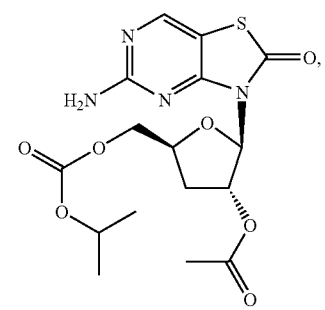

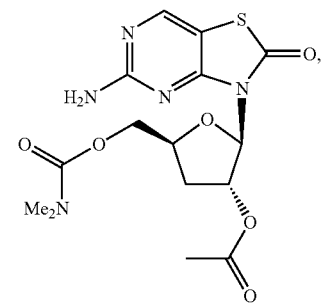

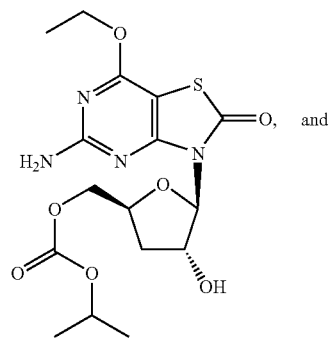

, and

-continued

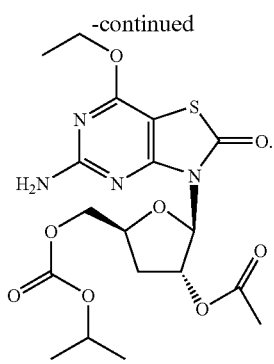

The invention is also directed to pharmaceutically acceptable salts, hydrates, and solvates of the Formula I compounds. Advantageous methods of making the compounds of the invention are also described.

The Formula I prodrugs are useful as immune system enhancers and have certain immune system properties including modulation, mitogenicity, augmentation, and/or potentiation or they are intermediates for compounds that have these properties. The compounds are expected to express effects on at least the natural killer, macrophages, dendritic or lymphocyte cells of the immune system of a host. Because of these properties they are useful as antiviral and antitumor agents or as intermediates for antiviral and antitumor agents. They can be used to treat an affected host by serving as the active ingredients of suitable pharmaceutical compositions.

In one aspect of the invention, Formula I prodrugs are utilized to treat the full range of viral diseases in mammals, including humans, by administering to the mammal a therapeutically effective amount of the compounds. Viral diseases contemplated to be treated with compounds of the invention include acute and chronic infections caused by both RNA and DNA viruses. Without limiting in any way the range of viral infections that may be treated, Formula I prodrugs are particularly useful in the treatment of infections caused by adenovirus, cytomegalovirus, hepatitis A virus (HAV), hepatitis B virus (HBV), flaviviruses including Yellow Fever virus and hepatitis C virus (HCV), herpes simplex type 1 and 2, herpes zoster, human herpesvirus 6, human immunodeficiency virus (HIV), human papilloma virus (HPV), influenza A virus, influenza B virus, measles, parainfluenza virus, poliovirus, poxvirus (including smallpox and monkeypox virus), rhinovirus, respiratory syncytial virus (RSV), multiple families of viruses that cause hemorrhagic fevers, including the Arenaviruses (LCM, Junin virus, Machup virus, Guanarito virus, and Lassa Fever), the Bunyaviruses (Hanta viruses and Rift Valley Fever) and Filoviruses (Ebola and Marburg virus), a range of viral encephalitides including West Nile virus, LaCrosse virus, California Encephalitis virus, Venezuelan Equine Encephalitis virus, Eastern Equine Encephalitis virus, Western Equine Encephalitis virus, Japanese Encephalitis virus, Kysanur Forest virus, and tickborne viruses such as Crimean-Congo Hemorrhagic fever virus.

In another aspect of the invention, Formula I prodrugs are utilized to treat bacterial, fungal, and protozoal infections in mammals by administering to the mammal a therapeutically effective amount of the compounds. The full range of pathogenic microorganisms is contemplated to be treatable by the compounds of the present invention, including without limitation those organisms that are resistant to antibiotics. The ability of compounds to activate multiple components of the immune system bypasses resistance mechanisms commonly found to reduce susceptibility to antibiotics, and thus treatment of infections in a mammal caused by such resistant microorganisms by Formula I prodrugs is a particular utility of the present invention.

In another aspect of the invention, Formula I prodrugs are utilized to treat tumors in mammals by administering to the mammal a therapeutically effective amount of the compounds. Tumors or cancers contemplated to be treated include but are not limited to those caused by virus, and the effect may involve inhibiting the transformation of virus-infected cells to a neoplastic state, inhibiting the spread of viruses from transformed cells to other normal cells, and/or arresting the growth of virus-transformed cells. The compounds of the invention are expected to be useful against a broad spectrum of tumors including but not limited to carcinomas, sarcomas, and leukemias. Included in such a class are mammary, colon, bladder, lung, prostate, stomach, and pancreas carcinomas and lymphoblastic and myeloid leukemias.

Another embodiment of the invention comprises treating abnormal cell growth by administering a therapeutically effective amount of a compound of the invention to a subject in need thereof. The abnormal cell growth can be a benign growth or a malignant growth. In particular, the abnormal cell growth can be a carcinoma, sarcoma, lymphoma, or leukemia. In one embodiment of this method, the abnormal cell growth is a cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. The method of the invention also comprises treating a patient having cancer wherein the cancer is selected from the group consisting of small cell lung carcinoma, non-small cell lung carcinoma, esophageal cancer, kidney cancer, pancreatic cancer, melanoma, bladder cancer, breast cancer, colon cancer, liver cancer, lung cancer, sarcoma, stomach cancer, cholangiocarcinoma, mesothelioma, or prostate cancer. In another embodiment of said method, said abnormal cell growth is a benign proliferative disease, including, but not limited to, psoriasis, benign prostatic hypertrophy or restenosis.

In another aspect of the invention, a method of treating a mammal comprises administering a therapeutically and/or prophylactically effective amount of a pharmaceutical containing a compound of the invention. In this aspect the effect may relate to modulation of some portion of the mammal's immune system, especially modulation of cytokine activities of Th1 and Th2, including but not restricted to the interleukin family, e.g., IL-1 through IL-12, and other cytokines such as TNF alpha, and interferons including interferon alpha, interferon beta, and interferon gamma, and their downstream effectors. Where modulation of Th1 and Th2 cytokines occurs, it is contemplated that the modulation may include stimulation of both Th1 and Th2, suppression of both Th1 and Th2, stimulation of either Th1 or Th2, and suppression of the other, or a bimodal modulation in which one effect on Th1/Th2 levels (such as generalized suppression) occurs at a high concentration, while another effect (such as stimulation of either Th1 or Th2 and suppression of the other) occurs at a lower concentration.

In another aspect of the invention, pharmaceutical compositions containing a Formula I prodrug are administered in a therapeutically effective dose to a mammal that is receiving anti-infective drugs not included in the compounds of the invention. In a preferred aspect of this invention, the pharmaceutical compositions containing a Formula I prodrug are administered in a therapeutically effective dose with anti-infective drug(s) that act directly upon the infectious agent to inhibit the growth of or kill the infectious agent.

In another aspect, the invention encompasses a method for treating or preventing hepatitis C virus infection in a mammal in need thereof, preferably in a human in need thereof.

In another aspect, the invention encompasses a method for treating or preventing hepatitis C virus infection in a patient in need thereof, comprising administering to the patient a therapeutically or prophylactically effective amount of a Formula I prodrug of the invention and a pharmaceutically acceptable excipient, carrier, or vehicle.

In a another aspect, the invention encompasses a method for treating or preventing hepatitis C virus infection in a patient in need thereof, comprising administering to the patient a therapeutically or prophylactically effective amount of a compound of a Formula I prodrug and an additional therapeutic agent, preferably an additional antiviral agent or anti-tumor agent as appropriate for the intended use.

In a preferred aspect of the invention, a pharmaceutical composition comprising a therapeutically effective amount of a Formula I prodrug provides for improved oral availability and administration as an immunomodulator. In another preferred aspect of the invention, a pharmaceutical composition comprising a therapeutically effective amount of a Formula I prodrug of the invention provides for masking the active structure as the agent passes through lymphoid tissue lining the stomach, thereby minimizing activation of this tissue and allowing for improved oral tolerability.

DETAILED DESCRIPTION OF THE INVENTION AND PREFERRED EMBODIMENTS

Where the following terms are used in this specification, they are used as defined below:

The terms "comprising" and "including" are used herein in their open, non-limiting sense.

The term "Formula I" refers to either the prodrugs and/or compounds depicted by the provided generic structure.

The term "pyrimidine" refers to nitrogenous monocyclic heterocycles.

The term "alkyl", as used herein, unless otherwise indicated, includes saturated monovalent hydrocarbon radicals having straight, branched, or cyclic (e.g., "cycloalkyl") moieties (including fused and bridged bicyclic and spirocyclic moieties), or a combination of the foregoing moieties. For an alkyl group to have cyclic moieties, the group must have at least three carbon atoms.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "Me" means methyl, "Et" means ethyl, "Ac" means acetyl, "Bz" means benzoyl, and "Tol" means toluoyl.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3 to 10 carbon atoms, preferably 5-8 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like. Illustrative examples of cycloalkyl are derived from, but not limited to, the following:

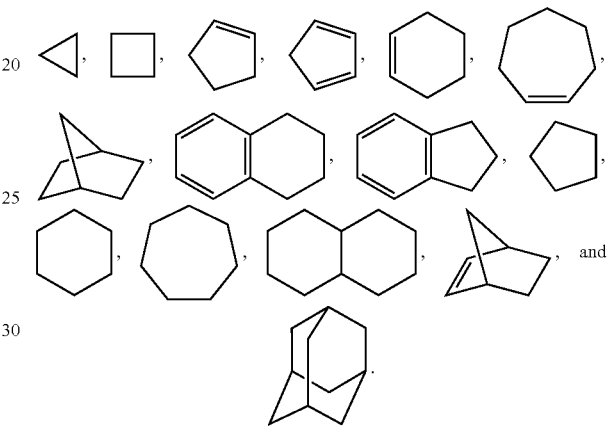

The term "aryl", as used herein, unless otherwise indicated, includes an organic radical derived from an aromatic hydrocarbon by removal of one hydrogen, such as phenyl or naphthyl.

The term "heterocyclyl" or "heterocyclic", as used herein, unless otherwise indicated, includes aromatic (e.g., a heteroaryl) and non-aromatic heterocyclic groups containing one to four heteroatoms each selected from O, S and N, wherein each heterocyclic group has from 4-10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The 4-10 membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other illustrative examples of 4-10 membered heterocyclic are derived from, but not limited to, the following:

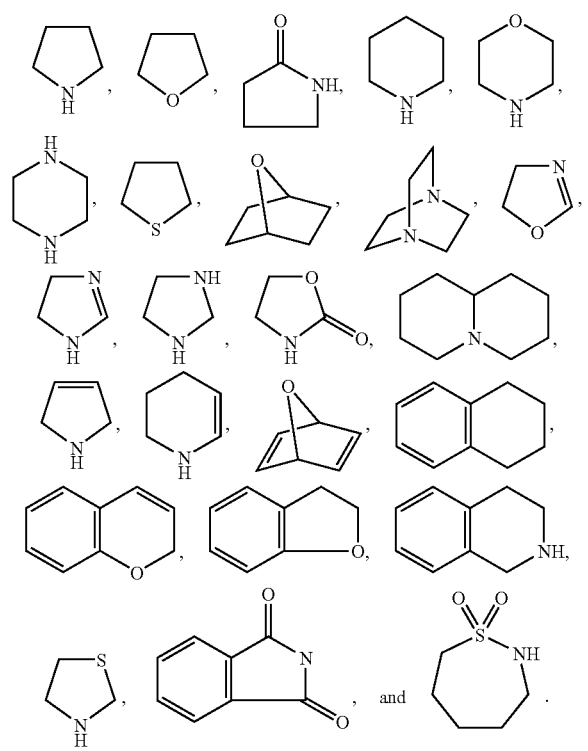

Unless defined otherwise, "alkyl," "alkenyl," "alkynyl," "aryl," "cycloalkyl," or "heterocyclyl" are each optionally and independently substituted by 1-3 substituents selected from alkylamine, amino, aryl, cycloalkyl, heterocyclyl, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms, carboxyl, cyano, halo, hydroxy, nitro, —C(O)OH, —C(O)$_2$—($C_1$-$C_6$ alkyl), —C(O)$_2$—($C_3$-$C_8$ cycloalkyl), —C(O)$_2$-(aryl), —C(O)$_2$-(heterocyclyl), —C(O)$_2$—($C_1$-$C_6$ alkyl)aryl, —C(O)$_2$—($C_1$-$C_6$ alkyl)heterocyclyl, —C(O)$_2$—($C_1$-$C_6$ alkyl)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkyl)aryl, —C(O)($C_1$-$C_6$ alkyl)heterocyclyl, and —C(O)($C_1$-$C_6$ alkyl)cycloalkyl, wherein each of these optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, e.g., $CF_3$.

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of HCV infection, the term "patient" or "subject" preferably means a monkey or a human, most preferably a human. In a specific embodiment the patient or subject is infected by or exposed to the hepatitis C virus. In certain embodiments, the patient is a human infant (age 0-2), child (age 2-17), adolescent (age 12-17), adult (age 18 and up) or geriatric (age 70 and up) patient. In addition, the patient includes immuno-compromised patients such as HIV positive patients, cancer patients, patients undergoing immunotherapy or chemotherapy. In a particular embodiment, the patient is a healthy individual, i.e., not displaying symptoms of other viral infections.

The term a "therapeutically effective amount" refers to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of infection, recurrence or spread of viral infection. A prophylactically effective amount may refer to an amount sufficient to prevent initial infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergies with another prophylactic or therapeutic agent.

The term "in combination" refers to the use of more than one prophylactic and/or therapeutic agents simultaneously or sequentially and in a manner that their respective effects are additive or synergistic.

The term "treating" refers to:
(i) preventing a disease, disorder, or condition from occurring in an animal that may be predisposed to the disease, disorder and/or condition, but has not yet been diagnosed as having it;
(ii) inhibiting the disease, disorder, or condition, i.e., arresting its development; and
(iii) relieving the disease, disorder, or condition, i.e., causing regression of the disease, disorder, and/or condition.

The terms "α" and "β" indicate the specific stereochemical configuration of a substituent at an asymmetric carbon atom in a chemical structure as drawn.

The compounds of the invention may exhibit the phenomenon of tautomerism. While the formula drawings cannot expressly depict all possible tautomeric forms, it is to be understood they are intended to represent any tautomeric form of the depicted compound and are not to be limited merely to a specific compound form depicted by the formula drawings. For example, it is understood for Formula I that regardless of whether or not the substituents are shown in their enol or their keto form, they represent the same compound (as shown in the example below).

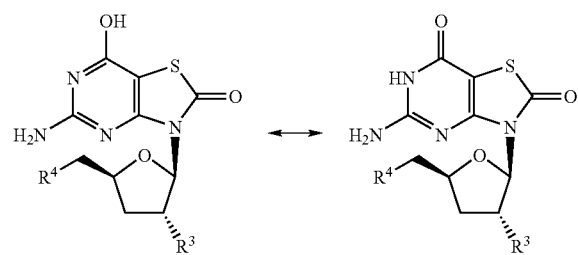

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, Formula I prodrugs are intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

"A pharmaceutically acceptable prodrug" is a compound that may be converted under physiological conditions or by solvolysis to the specified compound or to a pharmaceutically acceptable salt of such compound prior to exhibiting its pharmacological effect (s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared using methods known in the art, such as those described by *Burger's Medicinal Chemistry and Drug Chemistry*, 1, 172-178, 949-982 (1995). See also Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical & Biomedical Analysis*, 10, 601-605 (1992); and Prox et al., *Xenobiol.*, 3, 103-112 (1992).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Methods of Treatment and Prevention of Hepatitis C Viral Infections

The present invention provides methods for treating or preventing a hepatitis C virus infection in a patient in need thereof.

The present invention further provides methods for introducing a therapeutically effective amount of a Formula I prodrug into the blood stream of a patient in the treatment and/or prevention of hepatitis C viral infections.

The magnitude of a prophylactic or therapeutic dose of a Formula I prodrug or a pharmaceutically acceptable salt, solvate, or hydrate, thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to cancer patients, HIV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Doses

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lie preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture; alternatively, the dose of the compounds may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of Formula I prodrugs are exposed to the ligand and the magnitude of response is measured by an appropriate technique. The assessment of the compounds is then evaluated with respect to the compound potency, and the degree of conversion between the Formula I prodrug and its parent compound. Compounds for use in methods of the invention can be tested in suitable animal model systems prior to testing in humans, including but not limited to in rats, mice, chicken, cows, monkeys, rabbits, hamsters, etc. The compounds can then be used in the appropriate clinical trials.

The magnitude of a prophylactic or therapeutic dose of a Formula I prodrug or a pharmaceutically acceptable salt, solvate, or hydrate thereof in the acute or chronic treatment or prevention of an infection or condition will vary with the nature and severity of the infection, and the route by which the active ingredient is administered. The dose, and perhaps the dose frequency, will also vary according to the infection to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. Also, the dose may differ for various particular compounds of the invention; suitable doses can be predicted on the basis of the aforementioned in vitro measurements and on the basis of animal studies, such that smaller doses will be suitable for those compounds that show effectiveness at lower concentrations than other compounds when measured in the systems described or referenced herein. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 100 mg to 12 g per day, more preferably from 100 mg to 8000 mg per day.

Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered once time per week, two times per week, three times per week, four times per week or five times per week.

In a preferred embodiment, the compounds of the invention are administered to provide systemic distribution of the compound within the patient. In a related embodiment, the compounds of the invention are administered to produce a systemic effect in the body.

In another embodiment the compounds of the invention are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, β-interferons, alkylating agents, hormones or cytokines. In a preferred embodiment the invention encompasses the administration of an additional therapeutic agent that is HCV specific or demonstrates anti-HCV activity.

The Formula I prodrugs can be administered or formulated in combination with antibiotics. For example, they can be formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g. cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g. brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The Formula I prodrugs can also be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

The Formula I prodrugs can be administered or formulated in combination with an antidepressant. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The Formula I prodrugs can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

The Formula I prodrugs can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diprionate, amcinonide, beclomethasone dipropionate, betametasone, betamethasone benzoate, betamethasone diprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The Formula I prodrugs can be administered or formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, levovirin, viramidine and ribavirin, as well as foscarnet, amantadine, rimantadine, saquinavir, indinavir, amprenavir, lopinavir, ritonavir, the alpha-interferons; beta-interferons; adefovir, clevadine, entecavir, pleconaril.

The Formula I prodrugs can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloaminedes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g. Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g. Xanelim (Genentech)), and anti-B7 antibodies (e.g., IDEC-114 (IDEC)) and CTLA4-immunoglobulin. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (e.g., anti-IFN receptor antibodies, anti-IL-2 receptor antibodies (e.g. Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

The Formula I prodrugs can be administered or formulated in combination with an agent which inhibits viral enzymes, including but not limited to inhibitors of HCV protease, such as BILN 2061 and inhibitors of NS5b polymerase such as NM107 and its prodrug NM283 (Idenix Pharmaceuticals, Inc., Cambridge, Mass.).

The Formula I prodrugs can be administered or formulated in combination with an agent which inhibits HCV polymerase such as those described in Wu, *Curr Drug Targets Infect Disord.* 2003; 3(3):207-19 or in combination with compounds that inhibit the helicase function of the virus such as those described in Bretner M, et al., *Nucleosides Nucleotides Nucleic Acids.*, 22(5-8), 1531 (2003), or with inhibitors of other HCV specific targets such as those described in Zhang X., *IDrugs.*, 5(2), 154-8 (2002).

The Formula I prodrugs can be administered or formulated in combination with an agent which inhibits viral replication.

The Formula I prodrugs can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-alpha, and IFN-gamma).

The Formula I prodrugs can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

The Formula I prodrugs can be administered or formulated in combination with β-interferons which include, but are not limited to, interferon beta-1a, interferon beta-1b.

The Formula I prodrugs can be administered or formulated in combination with α-interferons which include, but are not limited to, interferon alpha-1, interferon alpha-2a (roferon), interferon alpha-2b, intron, Peg-Intron, Pegasys, consensus interferon (infergen) and albuferon.

The Formula I prodrugs can be administered or formulated in combination with an absorption enhancer, particularly those which target the lymphatic system, including, but not limited to sodium glycocholate; sodium caprate; N-lauryl-γ-D-maltopyranoside; EDTA; mixed micelle; and those reported in Muranishi *Crit. Rev. Ther. Drug Carrier Syst.*, 7-1-33, which is hereby incorporated by reference in its entirety. Other known absorption enhancers can also be used. Thus, the invention also encompasses a pharmaceutical composition comprising one or more Formula I prodrugs and one or more absorption enhancers.

The Formula I can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The Formula I prodrugs the other therapeutics agent can act additively or, more preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

In one embodiment, the methods of the invention comprise the administration of one or more Formula I prodrugs without an additional therapeutic agent.

Pharmaceutical Compositions and Dosage Forms

Pharmaceutical compositions and single unit dosage forms comprising a Formula I prodrug or a pharmaceutically acceptable salt, or hydrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, a pharmaceutical composition encompassed by this embodiment includes a Formula I prodrug or a pharmaceutically acceptable salt, or hydrate thereof, and at least one additional therapeutic agent. Examples of additional therapeutic agents include, but are not limited to, those listed above.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g. crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise compounds of the invention, or a pharmaceutically acceptable salt or hydrate thereof comprise 0.1 mg to 1500 mg per unit to provide doses of about 0.01 to 200 mg/kg per day.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent. Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophylized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof. Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g. *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985).

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions, sprays and aerosols, or other forms known to one of skill in the art. See, e.g. *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The compounds of the invention may also be administered directly to the lung by inhalation. For administration by inhalation, a compound of the invention or can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a compound directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a compound of the invention to the lung (see, e.g., Raleigh et al., *Proc. Amer. Assoc. Cancer Research Annual Meeting*, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a compound of the invention to the lung is a liquid spray device supplied, for example, by Aradigm Corporation. Liquid spray systems use extremely small nozzle holes to aerosolize liquid drug formulations that can then be directly inhaled into the lung.

In a preferred embodiment, a nebulizer device is used to deliver a compound of the invention to the lung. Nebulizers create aerosols from liquid drug formulations by using, for example, ultrasonic energy to form fine particles that can be readily inhaled (See e.g., Verschoyle et al., *British J. Cancer,* 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In a particularly preferred embodiment, an electrohydrodynamic ("EHD") aerosol device is used to deliver compounds of the invention to the lung. EHD aerosol devices use electrical energy to aerosolize liquid drug solutions or suspensions (see, e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of the compounds of the invention will be known to the skilled artisan and are within the scope of the invention.

Liquid drug formulations suitable for use with nebulizers and liquid spray devices and EHD aerosol devices will typically include a compound of the invention with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the compound. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. Nos. 5,112, 598; Biesalski, 5,556,611, which are herein incorporated by reference). A compound can also be formulated in rectal or vaginal compositions such as suppositories or retention enemas, e.g. containing conventional suppository bases such as cocoa butter or other glycerides.

In addition to the formulations described previously, a compound of the invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver the compounds of the invention. Certain organic solvents such as dimethylsulfoxide can also be employed, although usually at the cost of greater toxicity. The compounds of the invention can also be delivered in a controlled release system. In one embodiment, a pump can be used (Sefton, *CRC Crit. Ref Biomed Eng.,* 1987, 14, 201; Buchwald et al., *Surgery,* 1980, 88, 507; Saudek et al., *N. Engl. J. Med.,* 1989, 321, 574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.*, 1983, 23, 61; see also Levy et al., *Science*, 1985, 228, 190; During et al., *Ann. Neurol.*, 1989, 25, 351; Howard et al., 1989, *J. Neurosurg.* 71, 105). In yet another embodiment, a controlled-release system can be placed in proximity of the target of the compounds of the invention, e.g. the lung, thus requiring only a fraction of the systemic dose (see, e.g., Goodson, in *Medical Applications of Controlled Release*, supra, vol. 2, pp. 115 (1984)). Other controlled-release system can be used (see, e.g. Langer, *Science*, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a Formula I prodrug useful for the treatment or prevention of a Hepatitis C virus infection. In other embodiments, the invention provides a pharmaceutical pack or kit comprising one or more containers comprising a compound of the invention useful for the treatment or prevention of a Hepatitis C virus infection and one or more containers comprising an additional therapeutic agent, including but not limited to those listed above, in particular an antiviral agent, an interferon, an agent which inhibits viral enzymes, or an agent which inhibits viral replication, preferably the additional therapeutic agent is HCV specific or demonstrates anti-HCV activity.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The inventive agents may be prepared using the reaction routes and synthesis schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight.

Reagents were purchased from commercial suppliers such as Aldrich Chemical Company or Lancaster Synthesis Ltd. and were used without further purification unless otherwise indicated. All solvents were purchased from commercial suppliers such as Aldrich, EMD Chemicals or Fisher and used as received.

The reactions set forth below were done generally under a positive pressure of argon or nitrogen at an ambient temperature (unless otherwise stated) in anhydrous solvents, and the reaction flasks were fitted with rubber septa for the introduction of substrates and reagents via syringe. Glassware was oven dried and/or heat dried.

The reactions were assayed by TLC and/or analyzed by LC-MS and terminated as judged by the consumption of starting material. Analytical thin layer chromatography (TLC) was performed on glass-plates precoated with silica gel 60 $F_{254}$ 0.25 mm plates (EMD Chemicals), and visualized with UV light (254 nm) and/or iodine on silica gel and/or heating with TLC stains such as ethanolic phosphomolybdic acid, ninhydrin solution, potassium permanganate solution or ceric sulfate solution. Preparative thin layer chromatography (prepTLC) was performed on glass-plates precoated with silica gel 60 $F_{254}$ 0.5 mm plates (20×20 cm, from Thomson Instrument Company) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $MgSO_4$ prior to filtration and evaporation of the solvents under reduced pressure on a rotary evaporator and noted as solvents removed in vacuo. Column chromatography was completed under positive pressure using Merck silica gel 60, 230-400 mesh or 50-200 mesh neutral alumina, ISCO Flash-chromatography using prepacked RediSep silica gel columns, or Analogix flash column chromatography using prepacked SuperFlash silica gel columns. Hydrogenolysis was done at the pressure indicated in the examples or at ambient pressure.

$^1$H-NMR spectra and $^{13}$C-NMR were recorded on a Varian Mercury-VX400 instrument operating at 400 MHz. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

Infrared (IR) spectra were recorded on an ATR FT-IR Spectrometer as neat oils or solids, and when given are reported in wave numbers (cm$^{-1}$). Mass spectra reported are (+)-ES or APCI (+) LC/MS conducted by the Analytical Chemistry Department of Anadys Pharmaceuticals, Inc. Elemental analyses were conducted by the Atlantic Microlab, Inc. in Norcross, Ga. or by NuMega Resonance Labs, Inc. in San Diego, Calif. Melting points (mp) were determined on an open capillary apparatus, and are uncorrected.

The described synthetic pathways and experimental procedures utilize many common chemical abbreviations, 2,2-DMP (2,2-dimethoxypropane), Ac (acetyl), ACN (acetonitrile), Aliquat® 336 (trioctylmethylammonium chloride), Bn (benzyl), BnOH (benzyl alcohol), Boc (tert-butoxycarbonyl), Boc$_2$O (di-tert-butyl dicarbonate), Bz (benzoyl), CSI (chlorosulfonyl isocyanate), DAST (diethylaminosulfur trifluoride), DBU (1,8-diazabicyclo[5,4,0]undec-7-ene), DCC (N,N'-dicyclohexylcarbodiimide), DCE (1,2-dichloroethane), DCM (dichloromethane), DEAD (diethylazodicarboxylate), DIEA (diisopropylethylamine), DMA (N,N-dimethylacetamide), DMAP (4-(N,N-dimethylamino)pyridine), DMF (N,N-dimethylformamide), DMSO (dimethyl sulfoxide), EDC (1-(3-dimethylaminopropyl)-3-ethylcarbodiimide hydrochloride), Et (ethyl), EtOAc (ethyl acetate), EtOH (ethanol), Et$_2$O (diethyl ether), HATU (O-(7-azabenzotriazol-1-yl)-1,1,3,3-tetramethyluronium hexafluorophosphate), HBTU (O-benzotriazol-1-yl-N,N,N',N'-tetramethyluronium hexafluorophosphate), HF (hydrogen fluoride), HOAc (acetic acid), HOBT (1-hydroxybenzotriazole hydrate), HPLC (high pressure liquid chromatography), iPrOH (isopropyl alcohol), IPA (isopropyl alcohol), KHMDS (potassium bis(trimethylsilyl)amide), KN(TMS)$_2$ (potassium bis(trimethylsilyl) amide), KO$^t$Bu (potassium tert-butoxide), KOH (potassium hydroxide), LDA (lithium diisopropylamine), MCPBA (3-chloroperbenzoic acid), Me (methyl), MeCN (acetonitrile), MeOH (methanol), MTBE (methyl tert-butyl ether), NaCNBH$_3$ (sodium cyanoborohydride), NaH (sodium hydride), NaN(TMS)$_2$ (sodium bis(trimethylsilyl)amide), NaOAc (sodium acetate), NaOEt (sodium ethoxide), NIS (N-iodosuccinimide), Phe (phenylalanine), PPTS (pyridinium p-toluenesulfonate), PS (polymer supported), Py (pyridine), pyBOP (benzotriazol-1-yloxy)tripyrrolidinophosphonium hexafluorophosphate), TEA (triethylamine), TFA (trifluoroacetic acid), TFAA (trifluoroacetic anhydride), THF (tetrahydrofuran), TLC (thin layer chromatography), Tol (toluoyl), Val (valine), and the like.

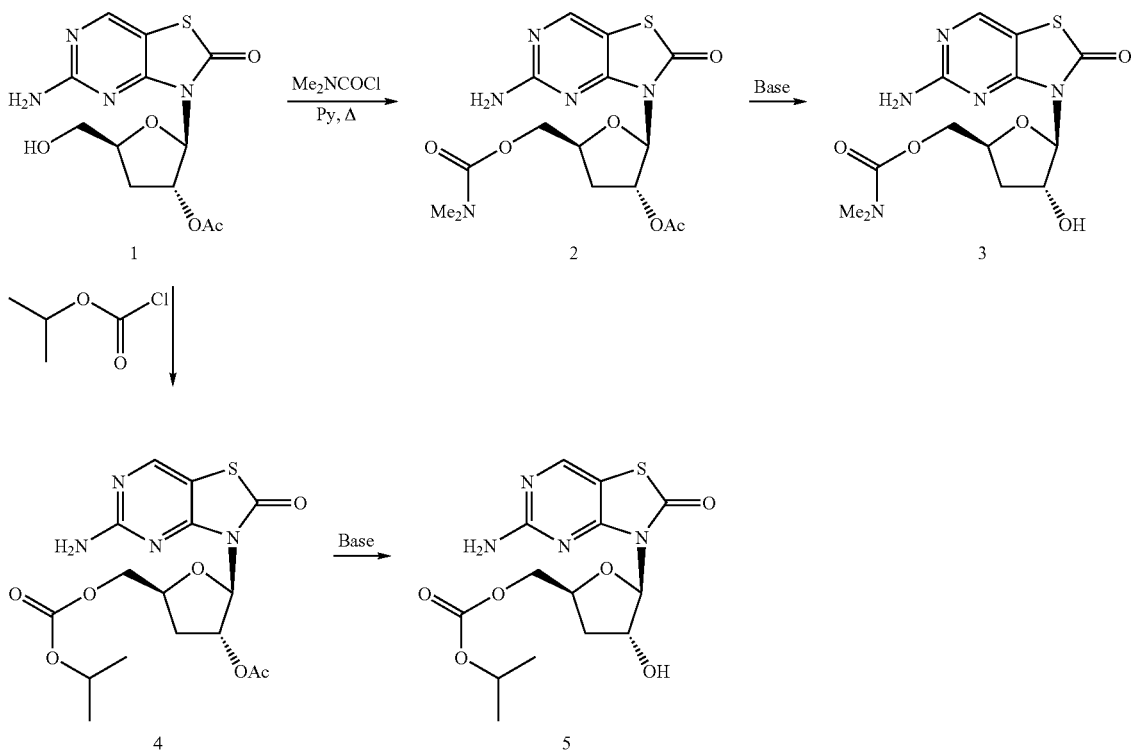

Scheme 1: 5'-Carbonates and Carbamates

5'-Carbamates of the invention can be prepared as shown in Scheme 1. The nucleoside 1 can be reacted with ClC(O)NR$^6$R$^7$, e.g., dimethylcarbamoyl chloride, to give the desired 5'-carbamate 2. The acetates can also be removed by treatment with base to give 3. Nucleoside 1 can also be reacted with isopropylcarbonyl chloride to give the desired carbonate 4. The acetates on 4 can be removed with base to give the 5'-carbonate 5.

Scheme 2: 2'-Carbamates and Carbonates

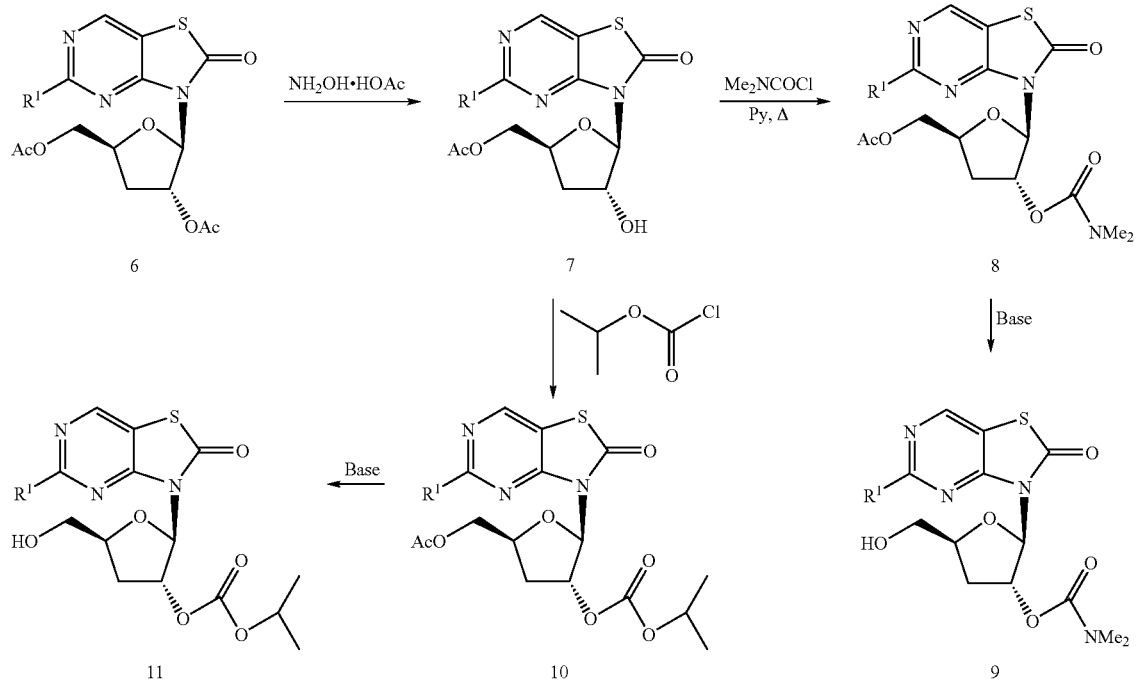

2'-Carbonates and carbamates can be prepared as shown in Scheme 2. The nucleoside 6 can be selectively hydrolyzed to the hydroxy compound 7. Alcohol 7 can be reacted with dialkylcarbamoyl chloride to give the desired 2'-carbamate 8. The acetates on 8 can be removed with base to give the 2'-carbamate 9. Further, alcohol 7 can be reacted with isopropylcarbonyl chloride to give the desired 2'-carbonate 10. The acetates on carbonate 10 can be removed by treatment with base to give the 2'-carbonate 11.

Scheme 3: Preparation of 6-Ether 5'-Carbonates

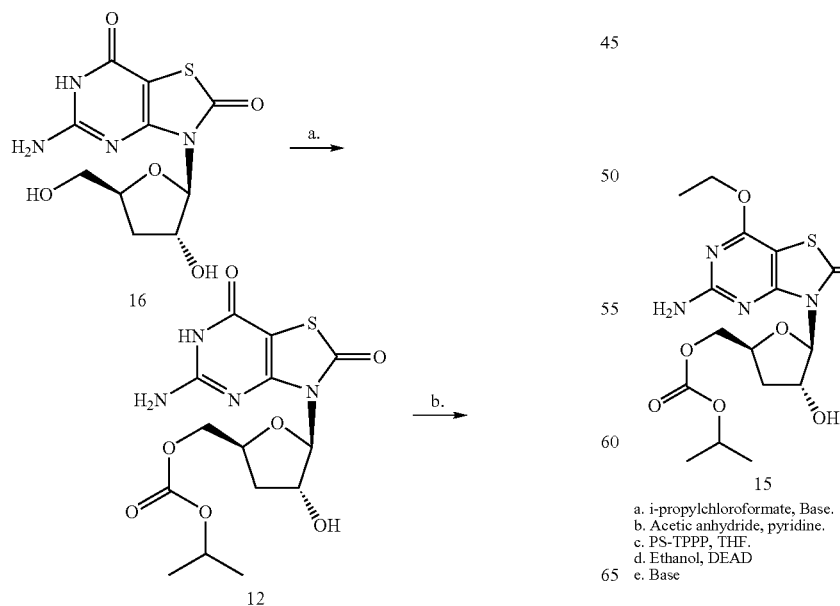

-continued

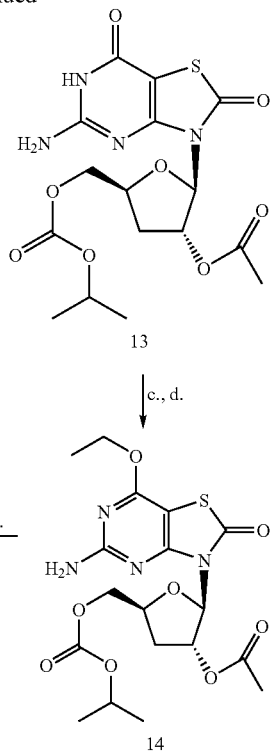

a. i-propylchloroformate, Base.
b. Acetic anhydride, pyridine.
c. PS-TPPP, THF.
d. Ethanol, DEAD
e. Base As shown in Scheme 3 the dihydroxy sugar can be selectively reacted with iso-propylchloroformate to form the 5'-carbonate 12 which can then be acetylated with acetic anhydride to form 13. The amide is then activated with polymer supported triphenylphosphine and subsequently treated with ethanol and DEAD to form the desired ether 14. The acetate can then be removed with a base treatment to form ether 15.

Example 1

Acetic acid 2-(5-amino-2-oxo-thiazolo[4,5-d]pyrimidin-3-yl)-5-isopropoxycarbonyloxymethyl-tetrahydro-furan-3-yl ester (4)

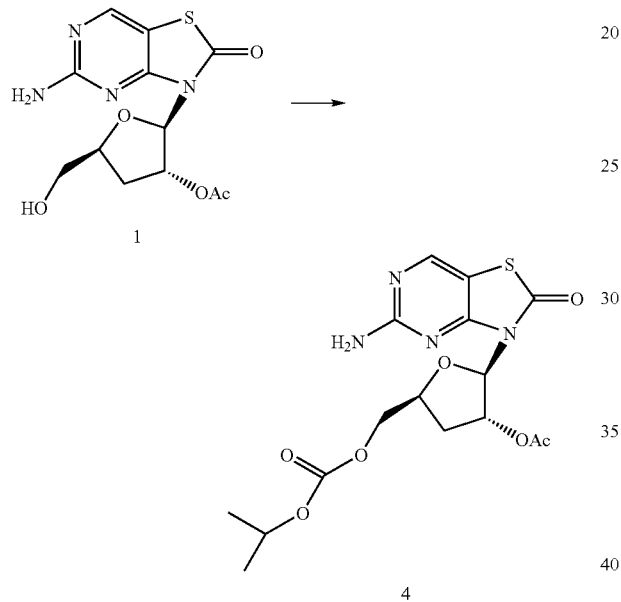

Compound 1 (1.50 g, 4.60 mmol; see International Publication No. WO 2006/066080, which is hereby incorporated herein by reference, pg. 56 (Example 3), for the synthesis of compound 1) was dissolved in pyridine (22.5 mL) and chilled to 0° C. Isopropylchloroformate (9.66 mL, 1 M in toluene, 9.66 mmol) was added, via syringe pump, over 45 min causing a change from colorless to an intense pink-orange. The reaction was allowed to warm to room temperature for 2 hr then 0° C. for 8 h. The reaction warmed to room temperature then poured into 500 mL of ice water. The water layer was decanted away from gooey precipitates. The precipitate was triturated 2× with DCM. The pure solids were collected via suction filtration, dried on high vacuum at 45° C. to yield 1.45 g (75%) of 4 as a white solid: $^1$H NMR (400 MHz, DMSO-$d_6$): 8.34 (H, s), 8.34 (11H, s), 6.90 (2H, s), 5.91 (1H, d, J=2.0 Hz), 5.65 (1H, d, J=7.7 Hz), 4.71 (1H, septet, J=6.2 Hz), 4.35-4.42 (1H, m), 4.28 (1H, dd, $J_1$=2.9 Hz, $J_2$=11.5 Hz), 4.07 (1H, dd, $J_1$=7.8 Hz, $J_2$=11.8 Hz), 2.63-2.71 (1H, m), 2.06-2.10 (1H, m), 2.06 (3H, s), 1.20 (3H, s), 1.18 (3H, s); [M+H]$^+$ at m/z 412.8. Analysis calc'd for $C_{16}H_{20}N_4O_7S$: C, 46.60; H, 4.89; N, 13.58; S, 7.77. Found: C, 46.23; H, 4.90; N, 13.45; S, 7.68.

Example 2

Carbonic acid 5-(5-amino-2-oxo-thiazolo[4,5-d]pyrimidin-3-yl)-4-hydroxy-tetrahydro-furan-2-ylmethyl ester isopropyl ester (5)

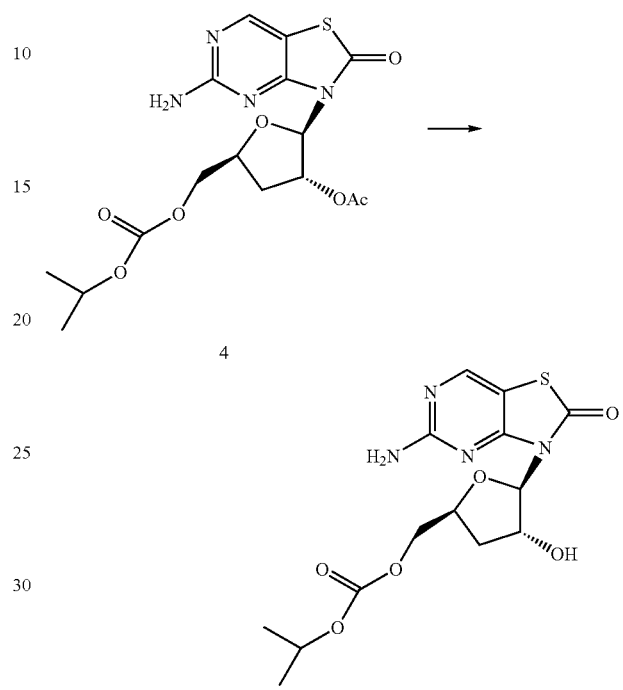

Compound 4 (0.50 g, 1.21 mmol) was dissolved in MeOH (5.0 mL) and TEA (0.51 mL, 3.63 mmol) was added. The solution was stirred at rt for 48 hr and warmed to 35° C. from 48 to 72 hr. The reaction was removed from heat, concentrated in vacuo, then submitted to flash chromatography (0-100% EtOAc-DCM) yielding 0.298 g (66%) of 5 as a white powder: $^1$H NMR (400 MHz, DMSO-$d_6$): 8.33 (1H, s), 6.85 (2H, bs), 5.85 (1H, d, J=2.3 Hz), 5.52 (1H, d, J=4.1 Hz), 4.79-4.83 (1H, m), 4.71 (1H, septet, J=6.2 Hz), 4.35-4.41 (1H, m), 4.23 (1H, dd, $J_1$=3.8 Hz, $J_2$=11.9 Hz), 4.06 (1H, dd, $J_1$=8.0 Hz, $J_2$=11.9 Hz), 2.40-2.47 (1H, m), 1.86-1.91 (1H, m), 1.20 (3H, d, J=1.4 Hz), 1.19 (3H, d, J=1.4 Hz); [M+H]$^+$ at m/z 370.9. Analysis calc'd for $C_{14}H_{18}N_4O_6S$: C, 45.40; H, 4.90; N, 15.13; S, 8.66. Found: C, 45.07; H, 4.84; N, 14.70; S, 8.51.

Anti-Viral Activity of Compounds

A number of assays may be employed in accordance with the present invention in order to determine the degree of anti-viral activity of a compound of the invention such as cell culture, animal models, and administration to human subjects. The assays described herein may be used to assay viral growth over time to determine the growth characteristics of a virus in the presence of a compound of the invention.

In another embodiment, a virus and a compound of the invention are administered to animal subjects susceptible to infection with the virus. The incidence, severity, length, virus load, mortality rate of infection, etc. can be compared to the incidence, severity, length, virus load, mortality rate of infection, etc. observed when subjects are administered the virus alone (in the absence of a compound of the invention). Anti-virus activity of the compound of the invention is demonstrated by a decrease in incidence, severity, length, virus load, mortality rate of infection, etc. in the presence of the compound of the invention. In a specific embodiment, the virus and the compound of the invention are administered to the animal subject at the same time. In another specific embodiment, the virus is administered to the animal subject before the compound of the invention. In another specific embodiment, the compound of the invention is administered to the animal subject before the virus.

In another embodiment, the growth rate of the virus can be tested by sampling biological fluids/clinical samples (e.g., nasal aspirate, throat swab, sputum, broncho-alveolar lavage, urine, saliva, blood, or serum) from human or animal subjects at multiple time points post-infection either in the presence or absence of a compound of the invention and measuring levels of virus. In specific embodiments, the growth rate of a virus is assayed by assessing the presence of virus in a sample after growth in cell culture, growth on a permissible growth medium, or growth in subject using any method well-known in the art, for example, but not limited to, immunoassay (e.g., ELISA; for discussion regarding ELISAs see, e.g. Ausubel et al., eds, 1994, Current Protocols in Molecular Biology, Vol. I, John Wiley & Sons, Inc., New York at 11.2.1), immunofluorescent staining, or immunoblot analysis using an antibody which immunospecifically recognizes the virus to be assayed or detection of a virus-specific nucleic acid (e.g., by Southern blot or RT-PCR analysis, etc.).

In a specific embodiment, viral titers can be determined by obtaining biological fluids/clinical samples from infected cells or an infected subject, preparing a serial dilution of the sample and infecting a monolayer of cells that are susceptible to infection with the virus (e.g. primary cells, transformed cell lines, patient tissue samples, etc) at a dilution of the virus that allows for the emergence of single plaques. The plaques can then be counted and the viral titer expressed as plaque forming units per milliliter of sample.

In one specific embodiment, the growth rate of a virus in a subject can be estimated by the titer of antibodies against the virus in the subject. Antibody serum titer can be determined by any method well-known in the art, for example, but not limited to, the amount of antibody or antibody fragment in serum samples can be quantitated by, e.g., ELISA. Additionally, in vivo activity of a Formula I compound can be determined by directly administering the compound to a test animal, collecting biological fluids (e.g., nasal aspirate, throat swab, sputum, broncho-alveolar lavage, urine, saliva, blood, or serum) and testing the fluid for anti-virus activity.

In embodiments where samples to be assayed for virus levels are biological fluids/clinical samples (e.g., nasal aspirate, throat swab, sputum, broncho-alveolar lavage, urine, saliva, blood, or serum), the samples may or may not contain intact cells. Samples from subjects containing intact cells can be directly processed, whereas isolates without intact cells may or may not be first cultured on a permissive cell line (e.g. primary cells, transformed cell lines, patient tissue samples, etc) or growth medium (e.g., LB broth/agar, YT broth/agar, blood agar, etc.). Cell suspensions can be cleared by centrifugation at, e.g. 300×g for 5 minutes at room temperature, followed by a PBS, pH 7.4 ($Ca^{++}$ and $Mg^{++}$ free) wash under the same conditions. Cell pellets can be resuspended in a small volume of PBS for analysis. Primary clinical isolates containing intact cells can be mixed with PBS and centrifuged at 300×g for 5 minutes at room temperature. Mucus is removed from the interface with a sterile pipette tip and cell pellets can be washed once more with PBS under the same conditions. Pellets can then be resuspended in a small volume of PBS for analysis.

In another embodiment, a compound of the invention is administered to a human subject infected with a virus. The incidence, severity, length, viral load, mortality rate of infection, etc. can be compared to the incidence, severity, length, viral load, mortality rate of infection, etc. observed in human subjects infected with a virus in the absence of a compound of the invention or in the presence of a placebo. Anti-viral activity of the compound of the invention is demonstrated by a decrease in incidence, severity, length, viral load, mortality rate of infection, etc. in the presence of the compound of the invention. Any method known in the art can be used to determine anti-viral activity in a subject such as those described previously.

Additionally, in vivo activity of a Formula I prodrug can be determined by directly administering the compound to an animal or human subject, collecting biological fluids/clinical samples (e.g., nasal aspirate, throat swab, sputum, broncho-alveolar lavage, urine, saliva, blood, or serum) and testing the biological fluids/clinical samples for anti-viral activity (e.g., by addition to cells in culture in the presence of the virus).

Metabolism of Formula I Prodrugs

The Formula I prodrugs of the present invention must be metabolized to 5-amino-3-(3'-deoxy-β-D-ribofuranosyl)-thiazolo[4,5-d]pyrimidin-2,7-dione (16) to serve as effective prodrugs.

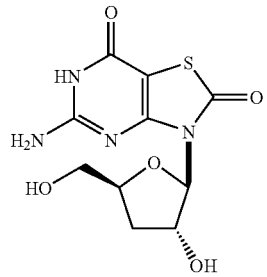

16

Hepatocyes often are used to assess the degree to which a compound may be transformed in the body of an animal, and it is known that such transformations may vary with hepatocytes from different species in a way that reflects metabolism in the whole animal. See Seddon T. et al., *Biochem Pharmacol.*, 38(10), 1657-65 (1989).

A study was undertaken to evaluate the metabolic stability of Formula I compounds 4 and 5 in the presence of fresh cynomolgus monkey hepatocytes and monitor the formation of 5-amino-3-(3'-deoxy-β-D-ribofuranosyl)-thiazolo[4,5-d] pyrimidin-2,7-dione (16) (see International Publication No. WO 2006/066080, which is hereby incorporated herein by reference, pg. 109 (synthesis thereof, Example 40) and pg. 137 (IFN-αproduction)). For comparison, the metabolic stability of famciclovir was also assessed.

Preparation of Fresh Hepatocyte Suspension

Fresh cynomolgus monkey hepatocyte suspension was purchased from CellzDirect (Tucson, Ariz.). Krebs-Henseleit buffer (KHB) was purchased from Sigma (St. Louis, Mo.).

The cynomolgus monkey hepatocyte suspension was prepared from fresh cynomolgus monkey hepatocytes in KBH at the concentration of 1.25 million cells/mL. The final incubation concentration (after test article addition) was 1.0 million cells/mL.

Preparation of Stock Solutions

DMSO stock solutions of 4 and 5 (10 mM) were prepared as follows:

|  | Compound: | |
|---|---|---|
|  | 4 | 5 |
| MW: | 412.42 | 370.38 |
| Purity: | 98% | 99% |
| Weight (mg): | 1.55 | 2.07 |
| DMSO (µL): | 368.3 | 553.3 |

Incubations

Reaction suspensions were prepared in removable 96-well tubes, each containing 320 µL of fresh cynomolgus monkey hepatocyte suspension at the density of 1.25 million cells per mL and 40 µL of KBH. The above mixtures were pre-incubated open at 37° C., 95% humidity and 5% $CO_2$ for 30 minutes. Reactions were initiated by the addition of 40 µL of test article at 10× concentration to each tube to achieve the final concentrations of 50 µM for the test article(s) and 1 million/mL cell density. The reaction suspension in each tube was mixed by inverting the tube several times. The tubes were incubated at 37° C. under 95% humidity and 5% $CO_2$.

Preparation of Samples for Analysis

At predetermined time points, reactions were terminated by transferring a 50-µL aliquot of the reaction suspension into a 96-well plate containing of 150 µL of the stop solution per well. The composition of the quenching solution was the following: acetonitrile containing 1 µg/mL nebularine as an internal standard and 0.1% formic acid.

The calibration curves were prepared in the following way: To 80 µL of cell suspension (at the cell density of 1.25 million/mL), 10 µL of KBH and 10 µL of the appropriate concentration of the compound in KBH were added. After mixing, 50 µL of each suspension was immediately transferred to 150 µL of the quenching solution in the 96-well plate.

All quenched samples were kept on wet ice until they were processed for analysis. They were then mixed using a bench top Multi-Tube Vortexer (VWR Scientific Products) for approximately 30 seconds, and centrifuged at 4,000 rpm (3,220 rcf) for 10 minutes at 4° C. Clear supernatant (100 µL) was transferred into a clean deep well 96-well plate, evaporated to dryness under nitrogen, reconstituted in 100 µL of 95:5 water:acetonitrile, and analyzed for the parent form and metabolites of the test article using an appropriate LC/MS/MS method.

Bioanalysis

The compounds were quantified on an API3000 LC/MS/MS instrument in the ESI-Positive MRM mode. A summary of the results of prodrug degradation and product generation is given in Table 1.

TABLE 1

Concentration of the Metabolized Product Formed in Cynomolgus Monkey Hepatocytes after 2 hrs Incubation of 50 µM of a Formula I Prodrug

| Formula I Compound | Metabolized Product | Product Concentration (µM) |
|---|---|---|
| 4 | 16 | 19.4 |
| 5 | 16 | 31.5 |
| Famciclovir | Penciclovir | 15.5 |

In fresh cynomolgus monkey hepatocytes compound 4 and 5 are metabolized to yield the corresponding 6-oxy metabolite 16 and famciclovir produces penciclovir.

Animal PK Experiments

Assessment of the ability of compounds of the present invention to deliver the parent compound to the systemic circulation after oral dosing was assessed by methods well known in the art. Each test compound can be formulated into a solution for oral dosing by dissolving the compound in either an aqueous buffer such as PBS at pH 3 or pH 7, in a solution of 100% propylene glycol, or in a solution containing a solubilizer such as Cremophor EL, Tween80, or PEG400. The solution of the compound is dosed by oral gavage to cynomolgus monkeys, generally using a group of four animals for each experiment. Plasma samples are collected from the animals at several time points (usually, from 6 to 12 time points were used) within 24 hours. The plasma samples are frozen quickly after collection, and thawed immediately before sample preparation for bioanalysis.

Bioanalysis

An aliquot (usually 50 µL) of each sample collected in animal PK studies or in vitro studies is quenched with acetonitrile (3:1 acetonitrile-to-plasma ratio) containing an internal standard (usually, nebularine). The suspension is centrifuged at 14,000 rpm for 5-10 min. An aliquot of the resulting supernatant is transferred into a clean vial and dried under nitrogen. The dried sample is reconstituted and submitted to LC-MS/MS analysis with MRM (multiple reaction monitoring) detection.

Calibration standards are prepared by serial dilution of an initial concentrated standard of the analyte with either animal plasma or cell culture media. Calibration standards are prepared for LC-MS/MS analysis as described above for animal PK samples. The LC-MS/MS analysis is performed in a batch mode with a combined calibration curve with at least two sets of calibration standards, bracketing the study samples. An LC-MS/MS trace for both the analyte and the internal standard is integrated, and the ratio of their peak areas is used to calculate a relative response of analyte in both the study samples and the calibration standards. The calibration curves are obtained by fitting the responses and standard concentrations of the calibrations standards to the simplest equation (i.e., linear or quadratic), with the simplest weighing factor (i.e., none, 1/x or $1/x^2$). The acceptance of the calibration curves is based on the accuracy of the back-calculated standard concentrations. A standard is accepted if the accuracy is within 15% for all the standards, except for the lower limit of quantitation for which 20% is applied. The fitted calibration curve is used to calculate the quantity of analyte in samples. The useful dynamic range of the calibration curve is 1-5 ng/mL to 2,000-10,000 ng/mL.

PK Calculations

The plasma concentration—time profile of the parent compound after oral administration of a known dose of the compound was used to calculate an AUC (area-under-the-curve) of 16 in systemic circulation. The AUC is normalized according to the total theoretical content of 16 based on molecular weight.

IFN-α Induction from Peripheral Blood Mononuclear Cells (PBMC)

Peripheral blood mononuclear cells (PBMCs) are prepared by standard methods from human blood and are primarily comprised of monocytes, NK cells, circulating dendritic cells and both T and B cells. Briefly, they are purified by density gradient centrifugation from a buffy coat, which is the component of whole blood that contains leukocytes and platelets. In turn, buffy coats are prepared by centrifuging whole blood and isolating the thin cream colored layer between the upper plasma layer and the lower red blood cell portion of the separated mixture.

PBMC Purification

Freshly collected donor buffy coats are obtained from the San Diego Blood Bank. PBMCs are isolated from the buffy coats using histopaque-1077 gradient (Sigma), essentially as described in the manufacturer's protocol. Buffy coats are transferred into 50 ml centrifuge tubes and PBS added to a total volume of 35 ml. Next 10 ml histopaque-1077 was underlayed at the bottom of each tube, which is then centrifuged at 259×g for 30 minutes at room temperature without brake in a 5804 R centrifuge (Eppendorf). The top PBS level from each tube is removed and discarded and the buffy coat layer transferred to a fresh tube. The total volume is made up to 50 ml with PBS and the tubes were then centrifuged for 10 minutes at 259×g at room temperature. The cells are washed an additional 3 times with PBS in this manner.

The cell (PBMC) pellet is then resuspended in 30-40 ml complete (RPMI 1640) media. PBMCs are seeded at either 2.5 or 7.5×10$^6$ cells/ml complete media (1× and 3× seedings, respectively) and allowed to rest overnight before compound exposure for 24 hours. The cells and media are then collected, centrifuged for 5 minutes at 735×g in a 5415 C microfuge (Eppendorf) at room temperature and the supernatant analyzed by IFN-α ELISA.

The ability of Formula I prodrugs to demonstrate favorable oral delivery characteristics and to induce immune responses when administered by a selected route can be compared with the results of similar experiments with compounds described in the literature. Hereby incorporated by reference in their entireties are U.S. Pat. Nos. 5,041,426 and 4,880,784, and U.S. patent application Ser. No. 10/861,430 (U.S. Patent Application Publication No. US 2005/0070556), now U.S. Pat. No. 7,321,033, and Ser. No. 11/304,691, filed Dec. 16, 2005, now U.S. Pat. No. 7,560,544, which disclose, inter alia, IFN-α induction of isatoribine.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

What is claimed is:

1. A compound of Formula I

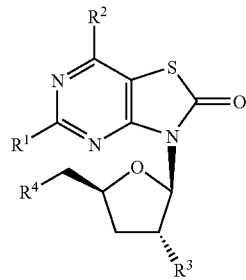

I wherein
$R^1$ is $NH_2$ or —N=CHNR$^6$R$^7$,
$R^2$ is H, OH, or —OR$^5$,
$R^3$ is OH, —OC(O)C$_1$-C$_{18}$alkyl, —OCO$_2$R$^5$, —OC(O)NR$^6$R$^7$, or a racemic, L-, or D-amino acid group —OC(O)CHR$^8$NHR$^9$,
$R^4$ is OH, —OC(O)C$_1$-C$_{18}$alkyl, —OCO$_2$R$^5$, —OC(O)NR$^6$R$^7$, or a racemic, L-, or D-amino acid group —OC(O)CHR$^8$NHR$^9$,
$R^5$ is —C$_1$-C$_7$alkyl,
$R^6$ and $R^7$ are independently —C$_1$-C$_7$alkyl or together with nitrogen atom to which they are attached form a 5- or 6-membered heterocyclic ring,
$R^8$ is H or —C$_1$-C$_7$alkyl,
$R^9$ is H, —C$_1$-C$_7$alkyl, —C(O)R$^5$, or —CO$_2$R$^5$,
wherein
at least one of $R^3$ or $R^4$ is —OCO$_2$R$^5$, —OC(O)NR$^6$R$^7$, or a racemic, L-, or D-amino acid group —OC(O)CHR$^8$NHR$^9$,
wherein the above alkyl is optionally substituted by 1-4 substituents selected from
hydrogen,
alkylamine,
amino,
aryl, cycloalkyl, heterocyclyl,
C$_1$-C$_6$ alkyl, C$_1$-C$_6$ haloalkyl, C$_1$-C$_6$ hydroxyalkyl, C$_1$-C$_6$ alkoxy, C$_1$-C$_6$ alkylamine, C$_1$-C$_6$ dialkylamine, C$_2$-C$_6$ alkenyl, or C$_2$-C$_6$ alkynyl, wherein each of which may be interrupted by one or more hetero atoms,
carboxyl,
cyano,
halo,
hydroxy,
mercapto,
oxo,
thioalkyl,
—C(O)$_2$—(C$_1$-C$_6$ alkyl), —C(O)$_2$-(aryl), —C(O)$_2$-(cycloalkyl), —C(O)$_2$-(heterocyclyl), —O—(C$_1$-C$_6$ haloalkyl), —O-aryl, —O-heterocyclyl, —NHC(O)—(C$_1$-C$_6$ alkyl), —NHC(O)—(C$_1$-C$_6$ alkenyl), —NHC(O)-(aryl), —NHC(O)-(cycloalkyl), —NHC(O)-(heterocyclyl), —NHS(O)$_2$—(C$_1$-C$_6$ alkyl), —NHS(O)$_2$-(aryl), —NHS(O)$_2$-(cycloalkyl), and —NHS(O)$_2$-(heterocyclyl),
wherein each of the above substituents can be further optionally substituted by 1-5 substituents selected from
amino,
C$_1$-C$_6$ alkylamine, C$_1$-C$_6$ dialkylamine,
C$_1$-C$_6$ alkyl, C$_1$-C$_6$ alkoxy, C$_1$-C$_6$ alkenyl, C$_1$-C$_6$ hydroxyl, and C$_1$-C$_6$ hydroxyalkyl, each optionally substituted by
cyano,
halo, and
nitro,
or a pharmaceutically acceptable salt or stereoisomer thereof.

2. The compound according to claim 1 wherein $R^1$ is $NH_2$.

3. The compound according to claim 2 wherein $R^2$ is H or OH.

4. The compound according to claim 3 wherein $R^3$ is —OCO$_2$R$^5$ or —OC(O)NR$^6$R$^7$ and $R^4$ is OH, —OC(O)C$_1$-C$_{18}$alkyl, —OCO$_2$R$^5$, or —OC(O)NR$^6$R$^7$.

5. The compound according to claim 3 wherein $R^4$ is —OCO$_2$R$^5$ or —OC(O)NR$^6$R$^7$ and $R^3$ is OH, —OC(O)C$_1$-C$_{18}$alkyl, —OCO$_2$R$^5$, or —OC(O)NR$^6$R$^7$.

6. The compound according to claim 1 selected from

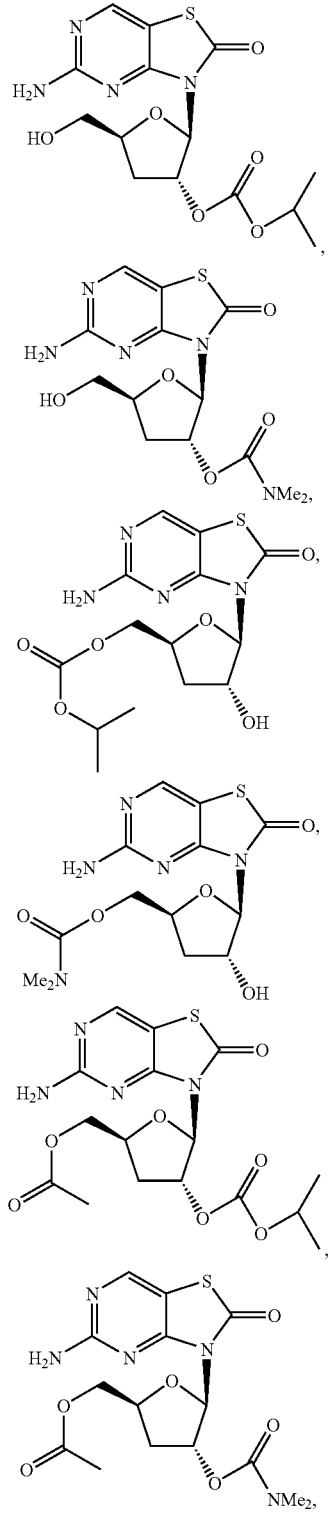

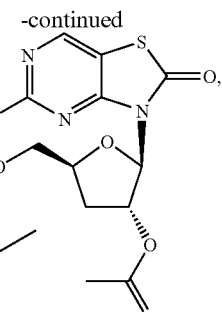

-continued

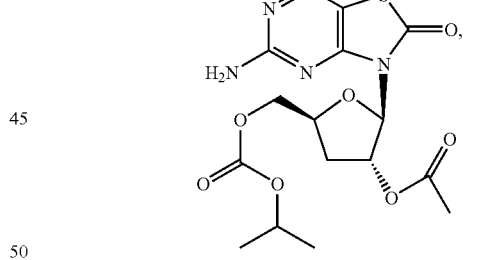

or a pharmaceutically acceptable salt or stereoisomer thereof.

7. A pharmaceutical composition comprising a pharmaceutically acceptable carrier and a compound according to claim 1.

8. A method of treating a hepatitis C virus infection in a patient infected with hepatitis C virus comprising:
administrating to the patient a therapeutically effective amount of a compound of claim 1.

* * * * *